(12) United States Patent
Mori

(10) Patent No.: US 9,060,899 B2
(45) Date of Patent: Jun. 23, 2015

(54) UNDERPANTS TYPE DISPOSABLE DIAPER AND METHOD FOR MANUFACTURING THE SAME

(75) Inventor: Yosuke Mori, Shikokuchuo (JP)

(73) Assignee: Daio Paper Corporation, Ehime (JP)

( * ) Notice: Subject to any disclaimer, the term of this patent is extended or adjusted under 35 U.S.C. 154(b) by 895 days.

(21) Appl. No.: 13/145,070

(22) PCT Filed: Jan. 18, 2010

(86) PCT No.: PCT/JP2010/050486
§ 371 (c)(1),
(2), (4) Date: Jul. 18, 2011

(87) PCT Pub. No.: WO2010/082651
PCT Pub. Date: Jul. 22, 2010

(65) Prior Publication Data
US 2011/0288517 A1 Nov. 24, 2011

(30) Foreign Application Priority Data
Jan. 19, 2009 (JP) ................ 2009-009035

(51) Int. Cl.
| A61F 13/15 | (2006.01) |
| A61F 13/49 | (2006.01) |
| A61F 13/496 | (2006.01) |

(52) U.S. Cl.
CPC ..... *A61F 13/49011* (2013.01); *A61F 13/15756* (2013.01); *A61F 13/15804* (2013.01); *A61F 13/496* (2013.01)

(58) Field of Classification Search
CPC ............ A61F 13/15756; A61F 13/15804; A61F 13/49011; A61F 13/49019; A61F 13/496; A61F 13/45699; A61F 13/84; A61F 13/49058; A61F 13/4906; A61F 13/49061
See application file for complete search history.

(56) References Cited

U.S. PATENT DOCUMENTS

| 4,036,233 A * | 7/1977 | Kozak ............... 604/370 |
| 6,110,157 A * | 8/2000 | Schmidt .......... 604/385.01 |

(Continued)

FOREIGN PATENT DOCUMENTS

| JP | 2006-204697 A | 8/2006 |
| JP | 3830901 A | 10/2006 |

(Continued)

*Primary Examiner* — Lynne Anderson
*Assistant Examiner* — Bradley Philips
(74) *Attorney, Agent, or Firm* — Arthur M. Reginelli; Renner Kenner

(57) ABSTRACT

To provide an underpants type disposable diaper that can be formed such that the edges of the leg openings fit the groin and gluteal portions of a wearer with no or less trim loss than conventional diapers The above problem is solved by that the ventral side outer sheet 12F and the back side outer sheet 12B each have a separated portion 12S formed by a slit or an elongated opening so as to extend in a width direction at a lengthwise middle section in a widthwise central region, a connecting member 12M connects the both outer sheets 12F, 12B at widthwise middle portions on the crotch side with respect to the separated portions, and the both outer sheets 12F, 12B are pulled up toward the waist side at entire widthwise sections on the waist side with respect to the separated portions 12S while being deformed with increased longitudinal separation distances of the separated portions 12S, and are diagonally pulled up toward the waist side at sections on the crotch side with respect to the separated portions 12S and at the same time, on both widthwise sides of connecting portions 12x connected to the connecting member, with increasing proximity to the both widthwise sides.

3 Claims, 11 Drawing Sheets

(56) References Cited

U.S. PATENT DOCUMENTS

| | | | |
|---|---|---|---|
| 2004/0039363 A1* | 2/2004 | Sugiyama et al. | 604/385.101 |
| 2004/0243081 A1* | 12/2004 | Suzuki et al. | 604/378 |
| 2005/0020992 A1* | 1/2005 | Van Gompel et al. | 604/385.01 |
| 2005/0177125 A1 | 8/2005 | Kondo et al. | |
| 2006/0244166 A1 | 11/2006 | Wada et al. | |
| 2009/0157029 A1* | 6/2009 | Hornung et al. | 604/367 |

FOREIGN PATENT DOCUMENTS

| | | |
|---|---|---|
| JP | 2007-524481 A | 8/2007 |
| WO | WO02/91968 A2 | 5/2002 |
| WO | WO2004/054490 A1 | 7/2004 |

* cited by examiner

UNDERPANTS TYPE DISPOSABLE DIAPER AND METHOD FOR MANUFACTURING THE SAME

TECHNICAL FIELD

The present invention relates to an underpants type disposable diaper and a method for manufacturing the same.

BACKGROUND ART

There is known an underpants type disposable diaper that is configured to include a barrel shaped abdomen portion formed by joining a ventral side outer sheet and a back side outer sheet at both sides; and an inner body for absorbing excrement that extends from a widthwise middle portion in an inner surface of the ventral side outer sheet to a widthwise middle portion in an inner surface of the back side outer sheet, the ventral side outer sheet and the back side outer sheet being not connected but separated at a crotch side. Such an outer sheet-split type diaper has an advantage that leg openings through which legs of a wearer are inserted do not need to be punched out or need to be punched out in smaller areas. That is, although cutout pieces for making the leg openings (hereinafter, referred to as trims) are generally disposed of, this type of a diaper can reduce material loss (hereinafter, referred to as trim loss).

FIG. 11 shows a flow of a process of manufacturing the outer sheet-spit type diapers. This manufacturing line is configured to convey diapers in a lateral direction such that a width of each diaper is oriented along a machine direction (MD) or a line flow direction. In this line, outer sheets 12F and 12B constituting an abdomen portion are formed, and an inner body 200 fabricated in another line is attached to the outer sheets 12F and 12B. For easy understanding, not separated members in the process of manufacture will be described using the same reference numerals as those given to the separated members in a finished product.

To describe in more detail, this manufacturing line mainly includes an elastic member attaching step 301, an elastic member cutting step 302, an outer sheet cutting/splitting step 304, an inner body attaching step 307, a folding step 308, a side portion joining step 309, and a separating step 310.

Specifically, at the elastic member attaching step 301, a band-like sheet base material 12 of a predetermined width is conveyed in a direction of continuation thereof while elongated elastic members 15 to 19 such as rubber threads are fixed in a state of being stretched in the MD direction to the almost entire band-like sheet base material 12 at intervals in a CD direction; and another band-like sheet base material 12 of a predetermined width is supplied and bonded to the top surface of the former sheet base material 12 in a direction of continuation thereof. In addition, if necessary, the elastic member cutting step 302 is performed to cut the elastic members 15, 16, 18, and 19 positioned in a section CT which will overlap the inner body 200, at predetermined intervals in the MD direction, using a cutting device such as a heat embosser or the like, so that the elastic members 15, 16, 18, and 19 do not act stretching force on the section CT.

Next, at the outer sheet cutting and splitting step 304, a predetermined middle portion SL in the CD direction of the band-like sheet base material 12 is cut by a slitter in the MD direction to split the sheet base material 12 into the portion to be the ventral side outer sheet 12F and the portion to be the back side outer sheet 12B; and a space between the outer sheets 12F and 12B is increased up to a predetermined distance. After the slitting, end edges 12L on the center side in the CD direction of the outer sheets 12F and 12B (constituting edges of leg openings LO) are cut off in a curved line.

After that, at the inner body attaching step 307, the inner body 200 fabricated in advance in another line is supplied at predetermined intervals in the MD direction, and is fixed to the portion to be the ventral side outer sheet 12F and to the portion to be the back side outer sheet 12B so as to straddle the two materials.

Then, at the folding step 308, the portion to be the ventral side outer sheet 12F and the portion to be the back side outer sheet 12B are folded in the CD direction such that surfaces thereof for attachment of the inner body 200 overlap each other. Next, at the side portion joining step 309, the portion to be the ventral side outer sheet 12F and the portion to be the back side outer sheet 12B are joined together at both ends of individual diapers. Then, at the separating step 310, the portion to be the ventral side outer sheet 12F and the portion to be the back side outer sheet 12B are cut at boundaries between individual diapers to thereby obtain individual diapers DP.

CITATION LIST

Patent Documents

Patent Document 1: WO 2004/054490 A1
Patent Document 2: JP 3830901 A

DISCLOSURE OF THE INVENTION

Technical Problems to be Solved

However, if an attempt is made to completely eliminate trim loss from an outer sheet-split type diaper, the diaper cannot be formed such that the edges of the leg openings fit the groin and gluteal portions of a wearer. Accordingly, it is not possible to manufacture an outer sheet-split type diaper without any trim loss, considering a fit to the circumferences of legs of a wearer.

Therefore, a main object of the present invention is to provide an underpants type disposable diaper that can be formed such that the edges of the leg openings fit the groin and gluteal portions of a wearer with no or less trim loss than conventional diapers, and a method for manufacturing the same.

Means to Solve the Problems

The present invention to solve the foregoing problem is as follows:

<Invention According to Claim 1>

An underpants type disposable diaper, comprising:

a barrel shaped abdomen portion that is formed by joining together a ventral side outer sheet and a back side outer sheet at both sides; and an inner body for absorbing excrement that is provided ranging from a widthwise middle portion in an inner surface of the ventral side outer sheet to a widthwise middle portion in an inner surface of the back side outer sheet, the ventral side outer sheet and the back side outer sheet being not connected but separated at a crotch side, wherein the ventral side outer sheet and the back side outer sheet each have a separated portion formed by a slit or an elongated opening so as to extend in a width direction at a lengthwise middle section in a widthwise central region, a connecting member connects the ventral side outer sheet at a widthwise middle portion on the crotch side with respect to the separated portion, to the back side outer sheet at a widthwise middle portion on the crotch side with respect to the separated portion, front and back end portions of the inner body are fixed to the ventral side outer sheet at a section on the waist side with respect to the separated portion, and to the back side outer sheet at a section on the waist side with respect to the separated portion, respectively and the ventral side outer sheet and the back side outer sheet are pulled up toward the waist side at entire widthwise sections on the waist side with respect to the separated portions while being deformed with increased longitudinal separation distances of the separated portions, and are diagonally pulled up toward the waist side at sections on the crotch side with respect to the separated portions and at the same time, on both widthwise sides of connecting portions connected to the connecting member, with increasing proximity to the both widthwise sides.

(Effect and Operation)

The underpants type disposable diaper is an outer sheet-split type but is configured in such a manner that: the ventral side outer sheet and the back side outer sheet each have a separated portion formed by a slit or an elongated opening so as to extend in the width direction at a lengthwise middle section in a widthwise central region; the ventral side outer sheet and the back side outer sheet are pulled up toward the waist side at entire widthwise sections on the waist side with respect to the separated portions while being deformed with increased longitudinal separation distances of the separated portions, and the ventral side outer sheet and the back side outer sheet are diagonally pulled up toward the waist side at sections on the crotch sides with respect to the separated portions and at the same time on both widthwise sides of the connecting portions connected to the connecting member, with increasing proximity to the both widthwise sides; and the outer sheets are kept in this state by a balance between the connection with the connecting member and the fixation to the inner body. In this state, the edges of the leg openings are formed by the diagonally extended portions so as to fit the groin and gluteal portions of a wearer. In addition, the diagonally extended portions can be formed solely by deformation with the separated portions, without the need to cut the outer sheets (alternatively, the diagonally extending portions can also be formed by cutting the outer sheets), as is understood from a later description of a manufacturing method. Accordingly, the underpants type disposable diaper can be shaped such that the edges of the leg openings fit the groin and gluteal portions of a wearer, with no or less trim loss than conventional diapers.

<Invention According to Claim 2>

The underpants type disposable diaper according to claim 1, wherein a first elongated elastic member is fixed in the width direction in a longitudinally stretched state to the ventral side outer sheet and the back side outer sheet on the waist side with respect to the separated portions, and a second elongated elastic member is fixed in a longitudinally stretched state to the ventral side outer sheet and the back side outer sheet in the width direction at positions overlapping the connecting portions and in the diagonal direction on the both sides of the connecting portions, on the crotch side with respect to the separated portions.

(Effect and Operation)

Since the diagonally extended portions constituting the edges of the leg openings are formed by the deformation with the separated portions, when the second elongated elastic member is simply fixed to the outer sheets in the width direction, the second elongated elastic member in the product state can be situated along the width direction at the positions overlapping the connecting portions and can be situated diagonally on the both sides of the connecting portions, that is, the second elongated elastic member can be situated along the leg openings, as is understood from the later description of the manufacturing method. This allows the diaper leg openings to fit favorably the circumferences of the legs of a wearer. In addition, although it is conventionally needed to fix the conventional elongated elastic member to the outer sheets along the leg openings while waving the elongated elastic member, the present invention makes it possible to manufacture an elastic member attachment structure so as to have the same advantage as before, without the need to introduce such a complicated manufacturing system.

<Invention According to Claim 3>

The underpants type disposable diaper according to claim 2, wherein the second elongated elastic member is thicker than the first elongated elastic member, and is fixed at a lower extension ratio than that of the first elongated elastic member.

(Effect and Operation)

If the second elongated elastic member is arranged along the diagonally extended portion, the second elongated elastic member has a longer path than that of the first elongated elastic member. Accordingly, it is preferred that the second elongated elastic member is made relatively low in extension ratio so as not to be too tight for the skin of a wearer, and is made relatively thick so as not to be decreased in a fit to the skin of a wearer due to the lower extension ratio.

<Invention According to Claim 4>

A method for manufacturing an underpants type disposable diaper having:

a barrel shaped abdomen portion that is formed by joining together a ventral side outer sheet and a back side outer sheet at both sides; and an inner body for absorbing excrement that is provided ranging from a widthwise middle portion in an inner surface of the ventral side outer sheet to a widthwise middle portion in an inner surface of the back side outer sheet, the ventral side outer sheet and the back side outer sheet being not connected but separated at a crotch side, the method comprising:

a separated portion forming step of feeding a band-like portion to be the ventral side outer sheet and a band-like portion to be the back side outer sheet in a direction of continuation thereof; and forming a separated portion as a slit or an elongated opening in the portion to be the ventral side outer sheet and in the portion to be the back side outer sheet so as to extend in an MD direction at a middle section in a CD direction of a central region in the MD direction;

a connecting step of, after the separated portion forming step, connecting, with a connecting member, the portion to be the ventral side outer sheet at a middle section in the MD direction on the center side in the CD direction with respect to the separated portion, to the portion to be the back side outer sheet at a middle section in the MD direction on a center side in the CD direction with respect to the separated portion;

a widening step of, after the connecting step, pulling up the portion to be the ventral side outer sheet and the portion to be the back side outer sheet, at entire sections in the MD direction on the outside in the CD direction with respect to the separated portions, and at sections on the center side in the CD direction with respect to the separated portions and at the same time on the both sides of connecting portions connected to the connecting member in the MD direction, toward the outside in the CD direction of the connecting portions connected to the connecting member; while the separated portions are deformed with increasing separation distances in the CD direction thereof, extending the portion to be the ventral side outer sheet and the portion to be the back side outer sheet, at the entire sections in the MD direction on the outside in the CD direction with respect to the separated portions, toward the outside in the CD direction, and extending diagonally the portion to be the ventral side outer sheet and the portion to be the back side outer sheet, at sections on the center side in the CD direction with respect to the separated portions and at the same time, on the both sides in the MD direction of the connecting portions connected to the connecting member, so as to come closer to the outside in the CD direction with increasing proximity to the both sides in the MD direction;

an inner body fabricating step of fabricating the inner body;

an inner body attaching step of, after the widening step, fixing front and back end portions of the inner body fabricated in the inner body fabricating step, to the portion to be the ventral side outer sheet at a section on the outside in the CD direction with respect to the separated portion and to the portion to be the back side outer sheet at a section on the outside in the CD direction with respect to the separated portion, respectively;

a folding step of, after the inner body attaching step, folding the portion to be the ventral side outer sheet and the portion to be the back side outer sheet in the CD direction, such that surfaces thereof for attachment to the inner body overlap; and a side portion joining/separating step of, after the folding step, joining together the portion to be the ventral side outer sheet and the portion to be the back side outer sheet, at both sides of individual diapers, and cutting the portion to be the ventral side outer sheet and the portion to be the back side outer sheet at boundaries of individual diapers, thereby to obtain individual diapers.

(Effect and Operation)

This manufacturing method provides the same operation and effect as those in the invention according in claim 1.

<Invention According to Claim 5>

The method for manufacturing an underpants type disposable diaper according to claim 4, wherein a first elongated elastic member is fixed in the MD direction in a longitudinally stretched state to the portion to be the ventral side outer sheet and the portion to be the back side outer sheet on the outside in the CD direction with respect to the separated portions, and a second elongated elastic member is fixed in the MD direction in a longitudinally stretched state to the portion to be the ventral side outer sheet and the portion to be the back side outer sheet on the center side in the CD direction with respect to the separated portions.

(Effect and Operation)

This manufacturing method provides the same operation and effect as those in the invention according in claim 2.

Effect of the Invention

According to the present invention as described above, there is an advantage of providing an underpants type disposable diaper that can be formed such that edges of leg openings fit in a curved line to the groin and gluteal portions of a wearer with no or less trim loss than conventional diapers, and a method for manufacturing the same, and the like.

BRIEF DESCRIPTION OF DRAWINGS

Figure 1:
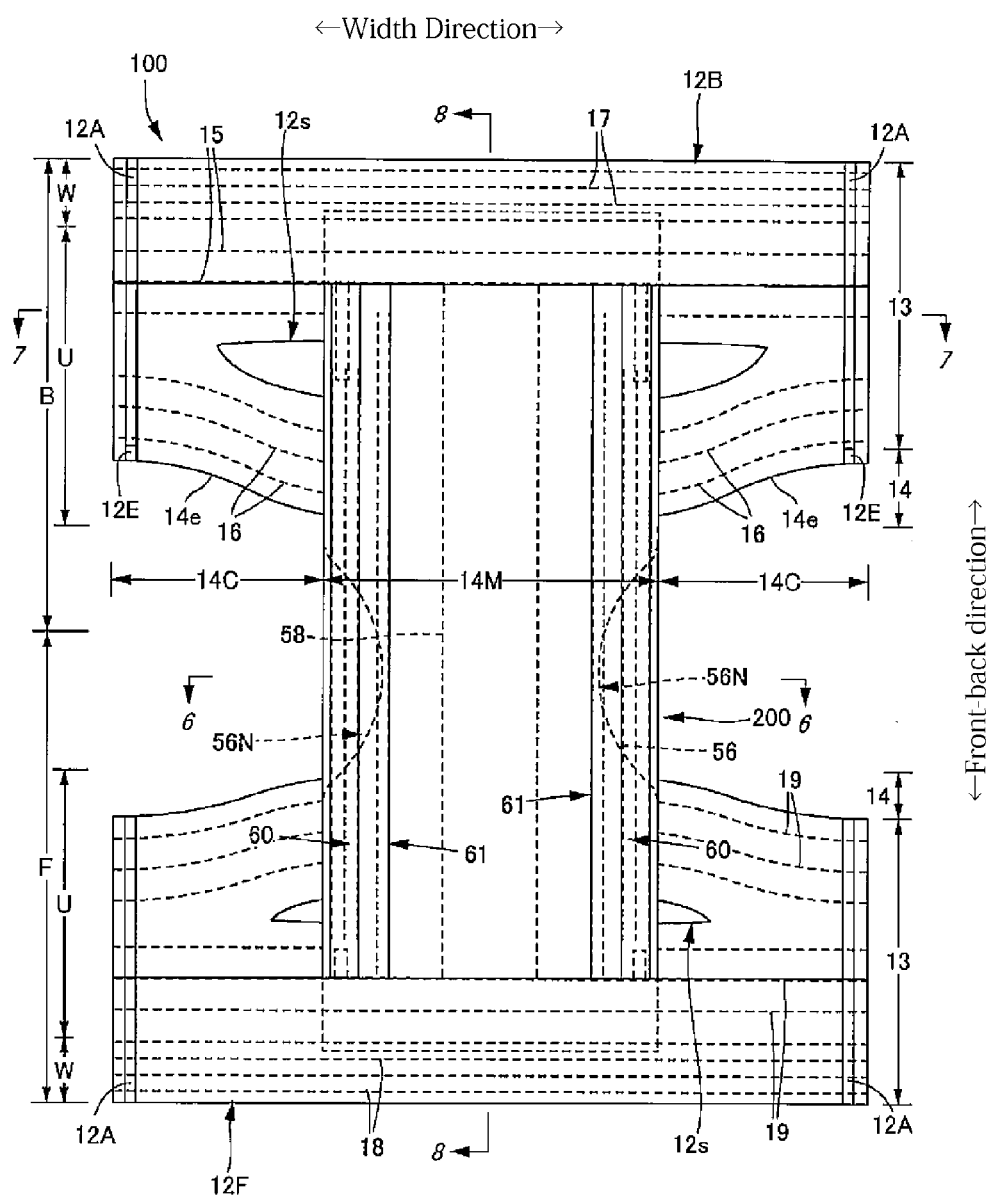
FIG. 1 is a plane view of an inner surface of an underpants type disposable diaper in an open state.
Figure 2:
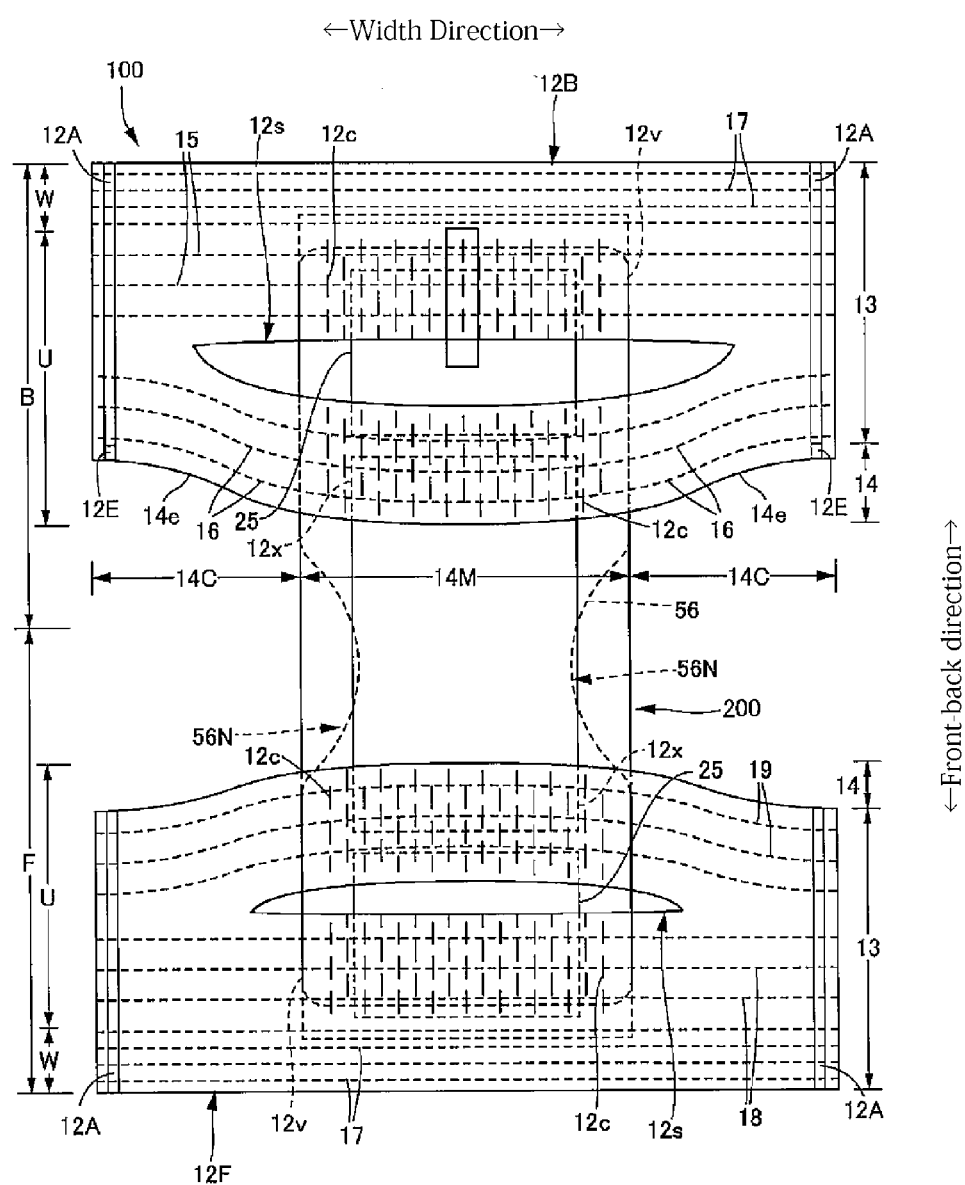
FIG. 2 is a plane view of an external surface of the underpants type disposable diaper in the open state.

An embodiment of the present invention will be described below in detail.

<Example of an Underpants Type Disposable Diaper>

FIGS. 1 to 9 show one example of an underpants type disposable diaper. In the following description, the term "front-back direction" refers to a direction that links a ventral side (front side) to a back side (rear side); the term "width direction" refers to a direction (right-left direction) orthogonal to the front-back direction; and the term "up-down direction" refers to a direction that becomes orthogonal to the circumference of an abdomen when the diaper is being used, that is, when the diaper is folded in two at a crotch portion such that a front portion and a back portion of the diaper overlap at both sides, in other words, a direction that links a waist opening WO to a crotch portion.

The underpants type disposable diaper has a ventral side outer sheet 12F covering a ventral side of an abdomen of a wearer, and a back side outer sheet 12B covering a back side of the same. The ventral side outer sheet 12F and the back side outer sheet 12B are entirely welded and joined together in the up-down direction at both widthwise side edges by heat sealing, ultrasonic welding or the like, thereby to form a barrel shaped abdomen portion 100. Reference numeral 12A denotes a welding portion, which constitutes a side seal section. As illustrated, if the back side outer sheet 12B extends under the welding portion 12A, the back side outer sheet 12B can be processed with heat sealing or the like uniformly in an up-down direction area containing such an extended portion, so that back side extended portions 14 can be provided with extended welding portions 12E.

In addition, in the abdomen portion 100, an inner body 200 is connected with a hot melt adhesive or the like at a front end portion thereof to an inner surface of a widthwise middle portion of the ventral side outer sheet 12F, and is connected with a hot-melt adhesive or the like at a back end portion thereof to an inner surface of a widthwise middle portion of the back side outer sheet 12B. The ventral side outer sheet 12F and the back side outer sheet 12B are not connected but separated from each other at the crotch side. A separation distance L8 may be about 150 to 250 mm.

Figure 7:
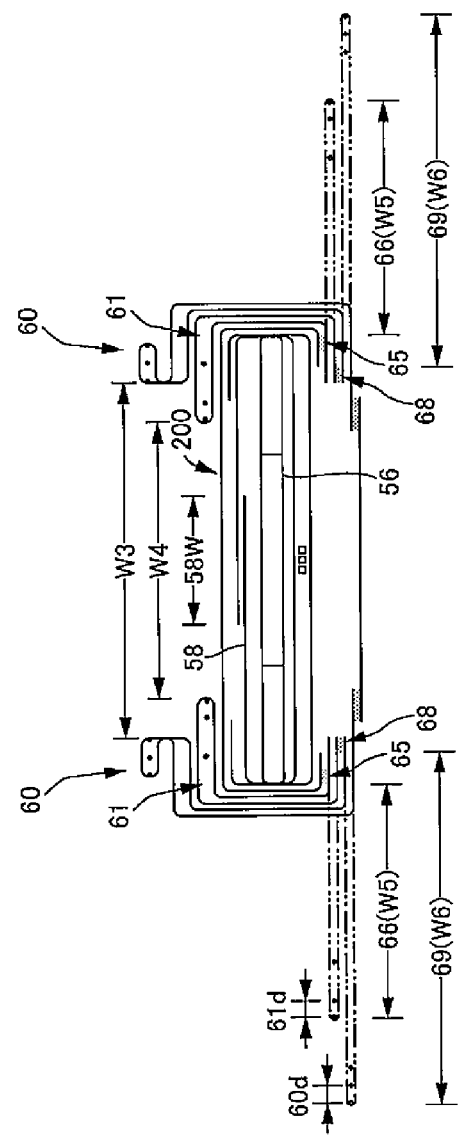
FIG. 7 is a cross-section view of the major components of the underpants type disposable diaper, with dimensions thereof.
Figure 8:
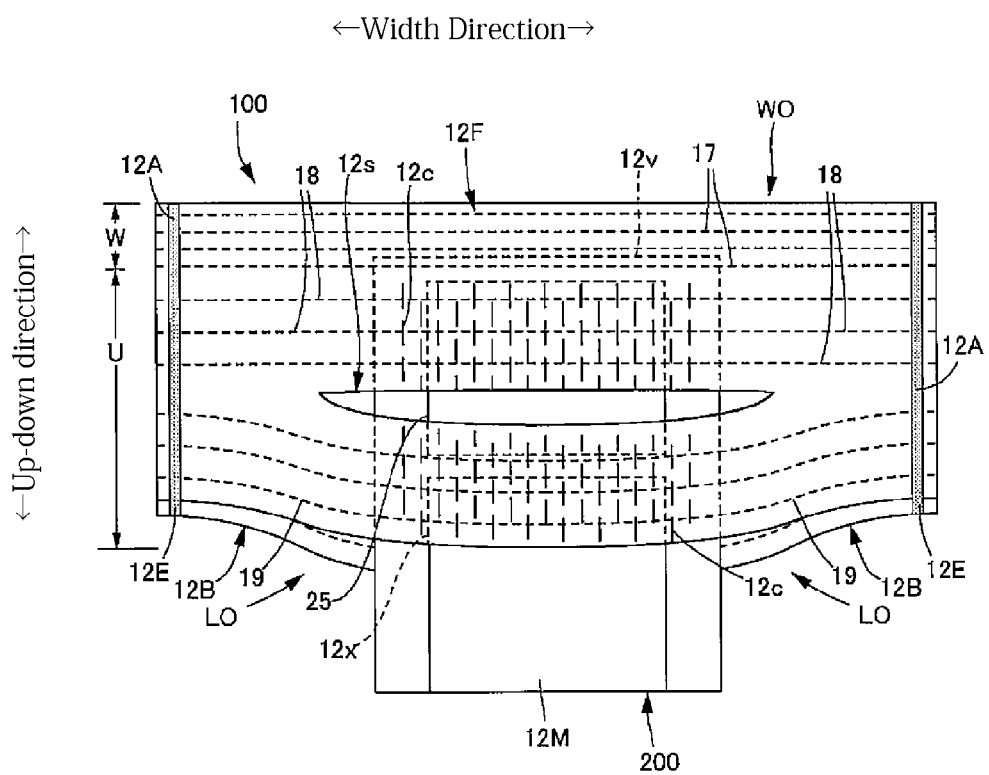
FIG. 8 is a front view of the diaper in a product state.
Figure 9:
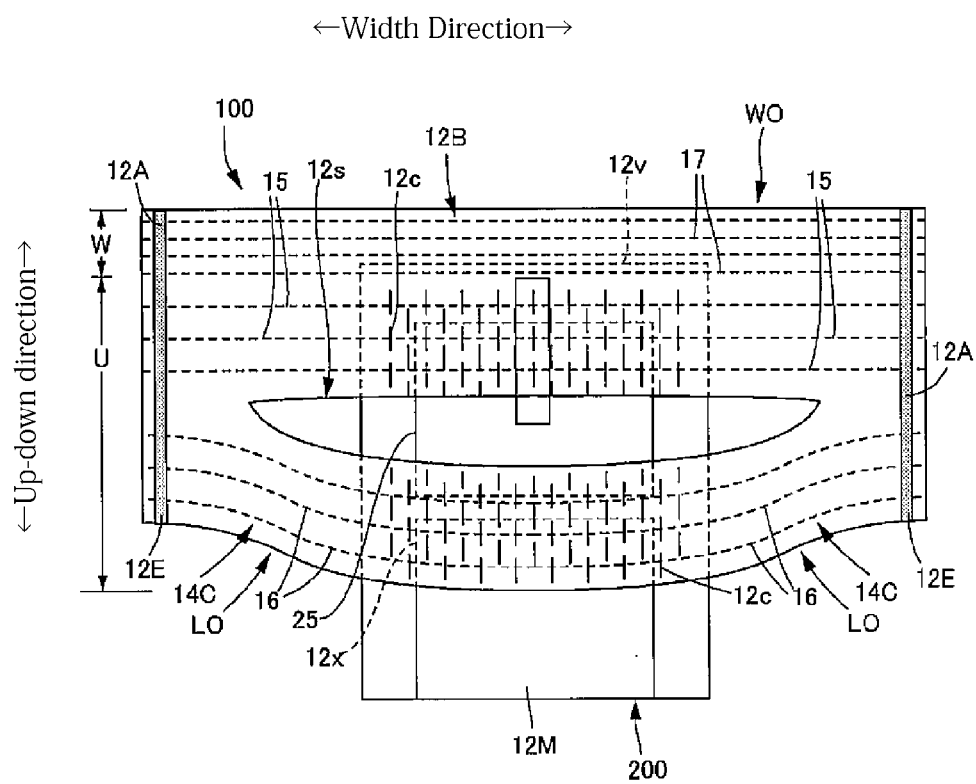
FIG. 9 is a rear view of the diaper in the product state.

As seen from FIGS. 7 and 8, an upper opening of the abdomen portion 100 constitutes the waist opening WO through which the abdomen of a wearer passes, and sections surrounded by a lower edge of the abdomen portion 100 and side edges of the inner body 200 on the both sides in the width direction constitute leg openings LO through which the legs of a wearer pass. The diaper is formed in the shape of a sand clock when the diaper is torn off at the welding portions 12A and opened as shown in FIG. 1. The inner body 200 extends and covers from the back side through the crotch portion to the ventral side, and is intended to receive excreted objects, and absorb and retain body liquids. The abdomen portion 100 is designed to hold the inner body 200 with respect to a wearer.

(Outer Sheet)

Figure 4:
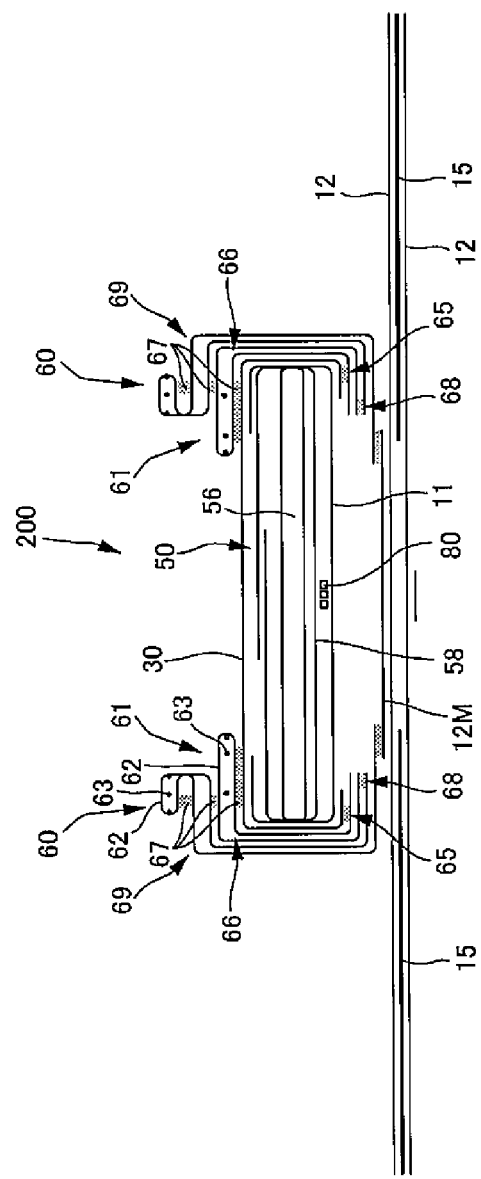
FIG. 4 is a cross-section view of FIG. 1 taken along a line 7-7.
Figure 5:
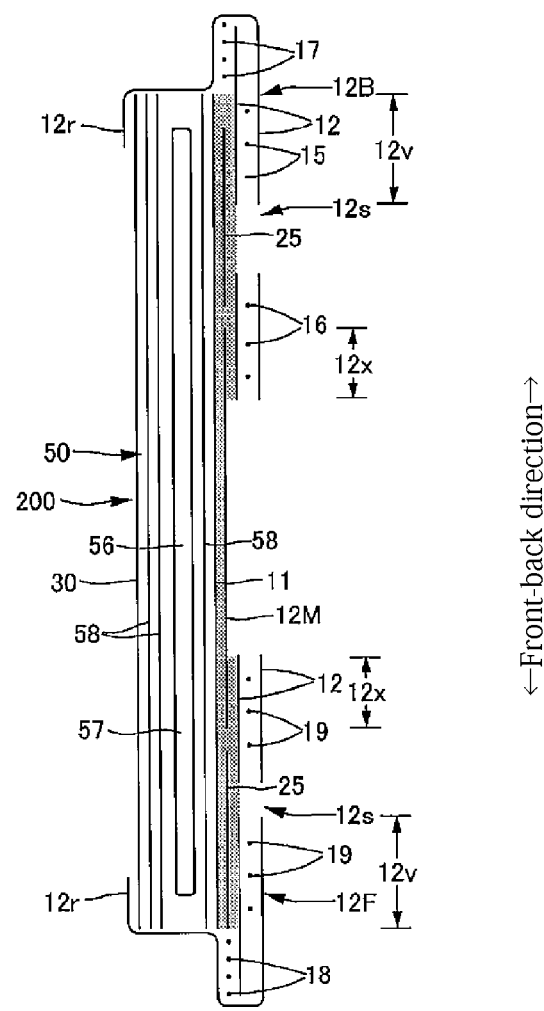
FIG. 5 is a cross-section view of FIG. 1 taken along a line 8-8.

The ventral side outer sheet 12F and the back side outer sheet 12B are each formed by sticking together two sheet base materials 12 and 12, as shown in FIGS. 4 and 5. The inner sheet base material 12 positioned on the inside of the outer sheet extends to the edge of the waist opening WO, whereas the outer sheet base material 12 positioned on the outside of the inner sheet wraps around the waist side edge of the inner sheet base material 12 and is folded back inside. A folded section 12r of the outer sheet material 12 extends so as to cover an upper side of the waist side edge of the inner body 200, and is fixed with a hot-melt adhesive or the like to an opposite surface. The sheet base materials 12 only need to be capable of being welded and have no particular limitation in other respects, but preferably use a nonwoven fabric. Such a nonwoven fabric has no particular limitation in raw fibers therefor. For example, the raw fibers may be any of synthetic fibers based on olefin such as polyethylene or polypropylene, polyester, polyamide or the like, recycled fibers such as rayon or cupra, natural fibers such as cotton or the like, mixed or composite fibers of two or more of the foregoing fibers. Further, the nonwoven fabric may be produced by any processing method. For example, the processing method may be any of known methods such as a spun lace method, spun bonding method, thermal bonding method, melt-blown method, needle punching method, air-through method, point bonding method, and the like. If any nonwoven fabric is used, the nonwoven fabric preferably has a fiber basis weight of about 10 to 30 g/m$^2$.

The ventral side outer sheet 12F and the back side outer sheet 12B each have separated portions 12S as slits or elongated openings so as to extend in the width direction at lengthwise middle portions of widthwise central regions. Although longitudinal positions of the separated portions 12S can be decided as appropriate, the separated portions 12S are desirably positioned on crotch portion sides with respect to centers in the front-back direction (longitudinal direction) of the outer sheets (ventral side outer sheet 12F and back side outer sheet 12B). Each of the separated portions 12S is preferably distant from the crotch portion side end edge of the outer sheet, by about 20 to 100 mm, more preferably about 30 to 60 mm. In addition, both widthwise ends of the separated portions 12S may be positioned on widthwise outside with respect to the both side edges of the inner body 200 or may be positioned on widthwise center side of the both side edges of the inner body 200. In the former case, openings can be formed in the outer sheets 12F and 12B on the both sides of the inner body 200 so as not to be covered or squeezed by the outer sheets 12F and 12B, which produces the advantage of providing a wearer with a comfortable wear feeling. In the latter case, there is an advantage of obtaining a diaper with the same appearance as conventional diapers.

Characteristically, a sheet-like connecting member 12M connects the ventral side outer sheet 12F at a widthwise middle portion on the crotch side with respect to the separated portion 12S, to the back side outer sheet 12B at a widthwise middle portion on the crotch side with respect to the separated portion 12S and front and back end portions of the inner body 200 are fixed to the ventral side outer sheet 12F at a section on the waist side with respect to the separated portion 12S, and to the back side outer sheet 12B at a section on the waist side with respect to the separated portion 12S, respectively. These connection and fixation can be conducted by appropriate joining means such as a hot-melt adhesive, heat sealing, or the like. The connecting portions are given reference numeral 12x, and the fixing portions are given reference numeral 12v.

In addition, the ventral side outer sheet 12F and the back side outer sheet 12B are pulled up toward the waist side at entire widthwise sections on the waist side with respect to the separated portions 12S while being deformed with increased longitudinal separation distances of the separated portions, and are diagonally pulled up toward the waist side at sections on the crotch side with respect to the separated portions 12S and at the same time, on both widthwise sides of connecting portions connected to the connecting member 12M, with increasing proximity to the both widthwise sides; and the outer sheets are kept in this state by a balance between the connection with the connecting member 12M and the fixation to the inner body 200.

Dimensions of the connecting portions 12x can be decided as appropriate. Preferably, width X1 of the same is about 30 to 70% of width X2 of the separated portions 12S, vertical length Y1 of the same is about 20 to 80% of the separation distance Y2 between the crotch side end edges of the outer sheets 12F and 12B and the crotch side end edges of the separated portions 12S, or is about 15 to 50 mm. In addition, the waist side end edges of the connecting portions 12x are preferably separated from the edges of the separated portions 12S and closer to the crotch sides. Further, dimensions of the fixing portions 12v with respect to the inner body 200 can be decided as appropriate, but preferably, width X3 of the same is larger than the width X1 of the connecting portions 12x.

Longitudinal separation distances (widthwise centers) of the separated portions 12S can be decided as appropriate. In the back side outer sheet 12B, if the longitudinal separation distance Y3 is relatively long, it is possible to form the edges of the leg openings LO at a deeper angle so as to easily fit the curved circumference of gluteal portion of a wearer, and it is possible to produce a large opening at a portion contacting the gluteal portion of a wearer, which is likely to come underneath the body of a wearer, thereby increasing comfort of the diaper in air permeability and flexibility. On the other hand, as for the separated portion 12S of the ventral side outer sheet 12F, if the longitudinal separation distance Y4 is made shorter, it is possible to form the edges of the leg openings LO at a shallower angle so as to easily fit the curve of the groin portion of a wearer, and it is possible to produce a smaller opening in the separated portion 12S if the opening of the separated portion 12S is in communication with the inside and the outside, whereby toes of a wearer are less prone to be caught in the opening while putting on the diaper. Therefore, Y3>Y4 holds preferably. In addition, using the manufacturing method described later, if the separated portions 12S formed in the back side outer sheet 12B and the ventral side outer sheet 12F have the same width X2, the longitudinal separation distances Y3 and Y4 become identical in length, and if the separated portions 12S formed in the back side outer sheet 12B and the ventral side outer sheet 12F are different in the width X2, the longitudinal separation distance Y3 or Y4 of the outer sheet with a larger width of the separated portion 12S become larger.

Meanwhile, for an enhanced fit at the abdomen portion, the ventral side outer sheet 12F and the back side outer sheet 12B have elongated elastic members 15 to 19 such as rubber threads at a predetermined extension ratio between the two sheet base materials 12 and 12. The elongated elastic members 15 to 19 may use synthetic rubber or natural rubber. Using a hot-melt adhesive or heat sealing or ultrasonic attachment, the two sheet base materials 12 and 12 can be attached together in the outer sheets 12F and 12B and the elongated elastic members 15 to 19 can be sandwiched and fixed between the sheet base materials 12 and 12. It is not preferred to fix the entire outer sheets 12F and 12B firmly because this deteriorates these sheets in hand feel. As a preferred combination, the elongated elastic members 15 to 19 are firmly attached and other parts are not attached or are weakly attached.

More specifically, the ventral side and back side outer sheets 12F and 12B have main portions 13 corresponding to up-down direction ranges of the side seal sections with the welding portions 12A constituted by welding points, and extended portions 14 extending under the main portions 13. The extended portions 14 have widthwise middle portions 14M overlapping the inner body 200, and have leg fit portions 14C extending from both sides of the widthwise middle portions 14M.

A shape of the extended portions 14 can be decided as appropriate. In the illustrated example, in the back side outer sheet 12B, the extended portion 14 has an upper end thereof extended under the back side main portion 13 with the same width as that of the back side main portion 13, and has a lower end thereof made narrower with increasing proximity to the crotch side. Meanwhile, in the ventral side outer sheet 12F, the extended portion 14 does not have any part identical in width to the main portion 13, and is made entirely narrower with increasing proximity to the crotch side. The extended portions 14 may be configured in the reverse of the foregoing arrangement or may be unified in shape adapted to either the back side or the ventral side. Since the crotch side edges of the extended portions form the edges of the leg openings LO, if the extended portions are configured as described above, the crotch side edge of the extended portion 14 in the ventral side outer sheet 12F fits to the groin portions of a wearer, and the crotch side edge of the extended portion 14 in the back side outer sheet 12B fits to the gluteal portion of a wearer, whereby the diaper can be entirely enhanced in fit the legs of a wearer.

Figure 6:
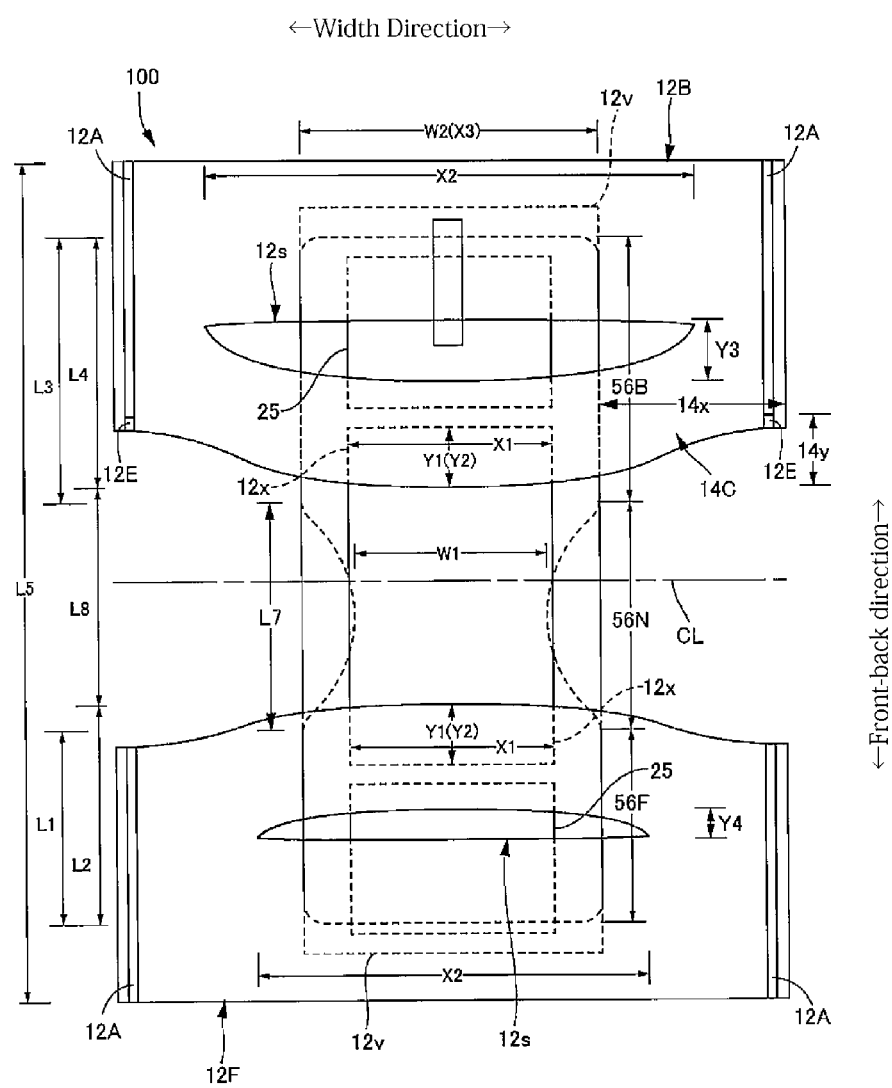
FIG. 6 is a plane view of major components of the underpants type disposable diaper in the open state, with dimensions thereof.

Dimensions of the extended portions 14 can be decided as appropriate. More preferably, as shown in FIG. 6, the leg fit portions 14C have a length 14x of 100 to 200 mm in the width direction (a maximum separation distance in the width direction between an outer edge 14e of the leg fit portion 14C and a side edge of the inner body 200 in the width direction), and the leg fit portions 14C have a length 14y of 30 to 80 mm in the up-down direction (an extended length) at the back side, and 10 to 60 mm at the ventral side. In addition, assuming that an area of a square defined by a widest side of the back side extended portion 14 in the width direction and a widest side of the back side extended portion 14 in the up-down direction is designated as S, the area of the back side extended portion 14 is preferably about 20 to 80% of S, in particular preferably about 40 to 60% of S, thereby achieving enhancement in outer appearance and fit. An area of the extended portion 14 in the ventral side outer sheet 12F is preferably 10 to 80%, more preferably 20 to 50%, of an area of the back side extended portion. An excessively large area of the ventral side extended portion is not preferred due to a deteriorated fit.

The main portions 13 are divided conceptually in the up-down direction into upper end portions (waist portions) W and lower portions U under the same. Although dimensions of these portions vary depending on the size of the diaper, the upper portions W may be 15 to 80 mm long in the up-down direction, and the lower portions U may be 35 to 220 mm long in the up-down direction.

In the upper end portions (waist portions) W of the main portions 13, a plurality of waist elastic members 17 are continuously fixed in the entire width direction between an inner surface of the inner sheet base material 12 and outer surfaces of folded sections 12r of the outer sheet base material 12, at up-down direction intervals therebetween and in a state of being extended in the width direction at a predetermined extension ratio. In addition, out of the waist elastic members 17, one or more members disposed in sections adjacent to the lower portions U of the main portions 13 may overlap the inner body 200, or may be disposed on both sides of the lower portions U in the width direction except for an central portion in the width direction overlapping the inner body 200. As the waist elastic members 17, about 3 to 22 rubber threads with a fineness of about 155 to 1,880 dtex, in particular about 470 to 1,240 dtex (in the case of synthetic rubber. For natural rubber, about 0.05 to 1.5 mm$^2$, particularly about 0.1 to 1.0 mm$^2$, in cross-section area), are preferably fixed at intervals of 4 to 12 mm at an extension ratio of about 150 to 400%, in particular about 220 to 320%. In addition, the waist elastic members 17 do not need to be all the same in fineness and extension ratio, and may be different in fineness and extension ratio between the upper and lower portions of the waist portion, for example.

In addition, in the lower portions U of the main portions 13, except for central portions overlapping the inner body 200 in the width direction, a plurality of first elongated elastic members 15 and 18 are entirely and continuously fixed in the width direction to sections above and on both sides of the central portions overlapping the inner body 200 in the width direction, on the waist side with respect to the separated portions 12S between an outer surface of the inner sheet base material 12 and an inner surface of the outer sheet base material 12, at up-down direction intervals therebetween and in a state of being extended in the width direction at a predetermined extension ratio.

As the first elongated elastic members 15 and 18, about 5 to 30 rubber threads with a fineness of about 155 to 1,880 dtex, in particular about 470 to 1,240 dtex (in the case of synthetic rubber. For natural rubber, about 0.05 to 1.5 mm$^2$, particularly about 0.1 to 1.0 mm$^2$, in cross-section area), are preferably fixed at intervals of 1 to 15 mm, in particular 3 to 8 mm, at an extension ratio of about 200 to 350%, in particular about 240 to 300%.

Further, in the lower portions U of the main portions 13, except for central portions overlapping the inner body 200 in the width direction, a plurality of second elongated elastic members 16 and 19 are entirely and continuously fixed in the width direction to sections (at least covering the entire leg fit portions 14C) on the both sides of the central portions overlapping the inner body 200 in the width direction, on the crotch side with respect to the separated portions 12S and between the outer surface of the inner sheet base material 12 and the inner surface of the outer sheet base material 12 in the extended portions 14, at up-down direction intervals and in a state of being extended at a predetermined extension ratio, along the crotch side edges of the extended portions 14 (that is, in the width direction at positions overlapping the connecting portions 12x and in the diagonal direction on the both sides of the connecting portions 12x).

As the second elongated elastic members 16 and 19, about 2 to 10 rubber threads with a fineness of about 155 to 1,880 dtex, in particular about 470 to 1,240 dtex (in the case of synthetic rubber. For natural rubber, about 0.05 to 1.5 mm$^2$, particularly about 0.1 to 1.0 mm², in cross-section area), are preferably fixed at intervals of 5 to 40 mm, in particular 5 to 20 mm, at an extension ratio of 150 to 300%, in particular 180 to 260%. Since paths of the second elongated elastic members 16 and 19 are longer than those of the first elongated elastic members 15 and 18, it is preferred that the second elongated elastic members 16 and 19 are made lower in extension ratio than the first elongated elastic members 15 and 18 so as not to become too tight for the skin of a wearer, and are made thicker than the first elongated elastic members 15 and 18 so as not to become lower in fit. However, the second elongated elastic members 16 and 19 may have an extension ratio which is equal to or larger than that of the first elongated elastic members 15 and 18, or may have a thickness which is identical to or thinner than that of the first elongated elastic members 15 and 18.

In the thus configured disposable diaper, the edges of the leg openings LO are formed by the diagonally extended portions on the both sides of the connecting portions 12x of the outer sheets 12F and 12B so as to fit the groin and gluteal portions of a wearer. In addition, as is understood from the later description of the manufacturing method, the diagonally extended portions can be formed by the deformation with the separated portions 12S without the need to cut the material, thereby producing no or less trim loss than conventional diapers. Alternatively, the edges of the leg openings LO can be made at a deeper angle, by performing a cutting operation in combination with the diagonally extended portions.

The elongated elastic members 15, 16, 18, and 19 are preferably provided in the lower portions U so as to act stretching force, except for the central portions that overlap the inner body 200 in the width direction, because the inner body 200 and the outer sheets 12F and 12B become less prone to be detached from each other. In this embodiment, the elastic members may exist only on the both sides in the width direction, or the elastic members may straddle the inner body 200 in the width direction from one to the other sides of the inner body 200, and be cut off at the central portion that overlaps the inner body 200 in the width direction so as to exert no stretching force (this is virtually equal to no provision of the elastic members). In the drawings, the cutting portions are shown with reference numeral 12c. Further, some or all of the elongated elastic members 15, 16, 18, and 19 may also straddle the inner body 200 in the width direction from one to the other sides of the inner body 200 so that stretching forces can act entirely on the back side main portions 13 and the back side extended portions 14 in the width direction.

(Connecting Member)

The connecting member 12M is preferably formed in the shape of a rectangle as in the illustrated embodiment, but may have any appropriate shape such as a sand-glass shape which is narrowed in a middle portion in the front-back direction, a barrel shape in which widths of front and back end portions are smaller than the middle portion in the front-back direction, a string shape, or the like. Also, a plurality of connecting members may be provided. A material for the connecting member 12M may be film or paper, but the connecting member 12M preferably uses a nonwoven fabric so as to cover the liquid impervious sheet 11, thereby obtaining a cloth-like hand feel. The connecting member 12M may use the same material as that for the ventral side outer sheet 12F and the back side outer sheet 12B. However, the connecting member 12M is preferably less prone to stretch in the front-back direction, and thus may use a material less prone to stretch in the front-back direction compared with the material for the ventral side outer sheet 12F and the back side outer sheet 12B.

Alternatively, the connecting member 12M may use a material different in function from that for the ventral side outer sheet 12F and the back side outer sheet 12B, such as a higher-strength material or a deodorant-contained material. Specifically, the connecting member 12M may use a spun-bonded nonwoven fabric, a melt-blown nonwoven fabric, a point-bonded nonwoven fabric, an air-through nonwoven fabric, an air-pointed nonwoven fabric, a spun-lace nonwoven fabric, an SMS nonwoven fabric, or the like, formed by PP, PP/PE, PP/PET fibers or the like, or any of the same containing a deodorant or the like.

In the illustrated example, if the connecting member 12M is exposed on the external surface of the inner body 200, a high pressure is applied to the connecting member 12M when a wearer is in a seated position. Accordingly, the connecting member 12M preferably uses a material with high fastness to rubbing (causing no fluff).

The connecting member 12M may be a sheet with design elements produced by printing or coloring. If such a sheet is to be used together with a design sheet 25 described later, these two sheets are preferably arranged such that design elements therein do not overlap. In the illustrated example, such overlapping does not occur because the connecting member is situated on the crotch side with respect to the separated portions 12S.

In the illustrated example, the connecting sheet 12M is sandwiched between the inner body 200 and the ventral side and back side outer sheets 12F and 12B in sections where the ventral side and back side outer sheets 12F and 12B and the inner body 200 overlap together. Alternatively, the connecting sheet 12M may be attached to the outside of the ventral side and back side outer sheets 12F and 12B.

(Design Sheet)

Since the separated portions 12S each have openings of a certain size, it is preferred that the openings of the separated portions 12S are partly or completely covered with the design sheet 25 so as not to expose any member on the back side (the liquid impervious sheet 11 in the illustrated example). The design sheet 25 is formed by printing design elements such as characters, patterns, or the like, on a sheet base material. The sheet base material may be paper or film, but is preferably a nonwoven fabric as with the connecting member 12x. If the openings of the separated portions 12S are covered with the design sheet 25, the design sheet 25 may be interposed between the outer sheets 12F and 12B and the inner body 200, but is preferably disposed on the external surface side of the outer sheets 12F and 12B.

(Inner Body)

Figure 3:
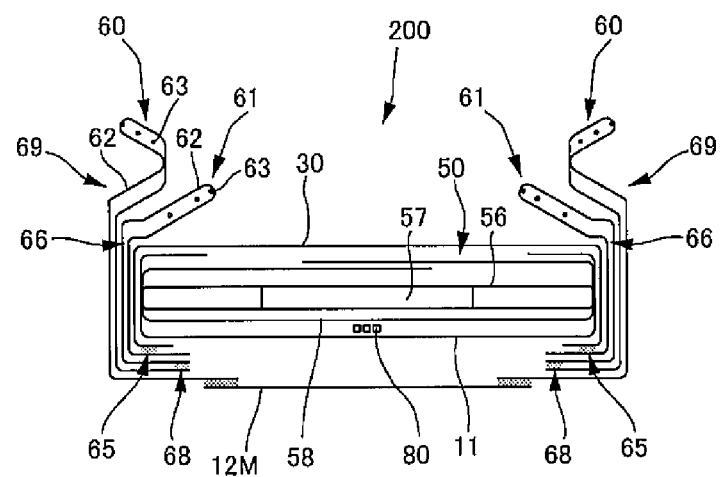
FIG. 3 is a cross-section view of FIG. 1 taken along a line 6-6.

The inner body 200 may have any shape, and is of a rectangle in the illustrated arrangement. As shown in FIG. 3, the inner body 200 includes a face sheet 30 facing the body of a wearer, a liquid impervious sheet 11, and an absorbent element 50 interposed between the two sheets. A cover sheet made of a nonwoven fabric may be fixed to the back side of the liquid impervious sheet 11 so as to cover the entire back side of the inner body 200 or to cover portions corresponding to the separated portions 12S, thereby to eliminate exposure of the liquid impervious sheet 11 on the back side of the diaper. In addition, the inner body 200 may have an middle sheet (second sheet) interposed between the face sheet 30 and the absorbent element 50 to quickly transfer a liquid having passed through the face sheet 30 to the absorbent element 50. However, for prevention of interference with heat transfer to the skin of a wearer, the inner body 200 preferably has no member between the face sheet 30 and the absorbent element 50, at least in a part of the inner body 200 overlapping a pocket portion 57 described later, preferably in the entire inner body 200. Further, in order to prevent leakage of excretion to the both sides of the inner body 200, barrier cuffs 60 and 61 may erect on the both sides of the inner body 200 so as to extend toward the body of a wearer. Although not shown, constituent members of the inner body 200 can be fixed as appropriate to each other by solid, bead, or spiral application of a hot-melt adhesive or the like.

(Face Sheet)

The face sheet 30 has a liquid pervious property. Therefore, a material for the face sheet 30 may be a porous or nonporous nonwoven fabric or a porous plastic sheet, for example. In addition, there is no particular limitation on raw fibers for use in such a nonwoven fabric. For example, the raw fibers may be any of synthetic fibers based on olefin such as polyethylene or polypropylene, polyester, polyamide or the like, recycled fibers such as rayon or cupra, natural fibers such as cotton or the like, mixed or composite fibers of two or more of the foregoing fibers. Further, the nonwoven fabric may be produced by any processing method. For example, the processing method may be any of known methods such as a spun lace method, spun bonding method, SMS method, thermal bonding method, melt-blown method, needle punching method, air-through method, point bonding method, and the like. In particular, to allow a temperature change to be easily perceived from the face side, nonwoven fabrics processed by the spun-bonding method and the SMS method are preferred for balanced thinness and strength, and nonwoven fabrics processed by the air-through method are preferred for achieving rapid absorption and a non-sticky feel with a low basis weight.

In addition, the face sheet 30 may be a single sheet or a layered sheet obtained by sticking two or more sheets to each other. Similarly, the face sheet 30 may be a single sheet or formed of two or more sheets in a planar direction.

If the face sheet 30 is formed from a nonwoven fabric, the nonwoven fabric preferably has a thickness of about 0.1 to 3 mm, in particular 0.5 mm or less, and a basis weight of about 10 to 40 $g/m^2$, in particular 25 $g/m^2$ or less, for excellent heat transfer from the backside to the skin of a wearer.

If the barrier cuffs 60 and 61 are arranged, it is preferred that the both side portions of the face sheet 30 extend to the back side of the absorbent element 50 between the liquid impervious sheet 11 and the barrier cuffs 60 and 61, and are attached to the liquid impervious sheet 11 and the barrier cuffs 60 and 61 with a hot-melt adhesive or the like for prevention of liquid infiltration. This brings about another advantage that the inner body 200 can be improved in stiffness at the both side portions.

(Liquid Impervious Sheet)

There is no particular limitation on a material for the liquid impervious sheet 11. For example, the material may be any of film materials of olefin resins such as polyethylene and polypropylene, a layered nonwoven fabric in which a nonwoven fabric is layered on a polyethylene sheet or the like, and a nonwoven fabric in which a water-proof film is interposed for virtual liquid imperviousness (in this case, the water-proof film and the nonwoven fabric constitute a liquid impervious sheet). As a matter of course, in addition to the foregoing examples, there are liquid impervious, moisture pervious sheets that have been favorably used in recent years from the viewpoint of prevention of stuffiness. Such a sheet made of a liquid impervious and moisture pervious material may be a microporous sheet obtained by melting and kneading an inorganic filling agent into an olefin resin such as polyethylene or polypropylene to thereby form a sheet and then extending the sheet in a uniaxial or biaxial direction, for example. Further, the liquid impervious sheet 11 may use a sheet that is given liquid imperviousness without the use of a water-proof film, by using a nonwoven fabric of micro denier fibers, applying heat or pressure to make gaps in fibers smaller with enhanced leakage resistance, coating with high water-absorption resin or hydrophobic resin, or applying a water repellent agent.

For an enhanced leakage preventing property, the liquid impervious sheet 11 preferably wraps around the both sides of the absorbent element 50 and extends to the both side portions of the absorbent element 50 on the face sheet 30 side. An appropriate width of the extended portion is about 5 to 20 mm on both of the right and left sides.

The liquid impervious sheet 11 may also have designed patterns prepared by printing or coloring on the inner or outer surface. In addition, the liquid impervious sheet 11 may have a printed or colored design sheet attached to the outer surface, as a member different from the crotch outer sheet 12M. Further, the liquid impervious sheet 11 may has inside an excretion indicator 80 that changes in color when contacting a liquid. The excretion indicator 80 is preferably interposed between the liquid impervious sheet 11 and the absorbent body 56. The excretion indicator 80 preferably covers 30% or more of the entire length of the absorbent body 56, in particular preferably 60% or more of the same. The excretion indicator 80 is preferably provided at least along the widthwise center of the absorbent body 56. If the absorbent body 56 is wrapped with a covering sheet 58 described later, the excretion indicator 80 may be positioned on the absorbent body 56 side or the liquid impervious sheet 11 side of the covering sheet 58. Alternatively, another member having the excretion indicator 80 may be interposed between the liquid impervious sheet 11 and the absorbent body 56.

(Barrier Cuffs)

Barrier cuffs 60 and 61 are band-like members that extend in the entire front-back direction along the both sides of the inner body 200. The barrier cuffs 60 and 61 are provided to block urine or loose stool moving laterally over the face sheet 30 and to prevent lateral leakage.

In this embodiment, double barrier cuffs 60 and 61 are disposed on each of the right and left sides of the inner body 200, as shown in FIGS. 3 and 4. In the open diaper, the inner barrier cuffs 61 erect so as to extend diagonally from the side portions toward the central portion of the inner body 200 in the width direction. The outer barrier cuffs 60 erect so as to extend from the side portions of the inner body 200 on the outer side of the inner barrier cuffs 61 in the width direction, root sections thereof erect diagonally so as to extend toward the central portion of the inner body 200 in the width direction, and central to leading end portions thereof erect diagonally so as to extend outward in the width direction.

More specifically, the inner barrier cuffs 61 are each configured in such a manner that a band-like barrier sheet 62 being the same in length as the inner body 200 in the front-back direction, is folded back and doubled in the width direction, and a plurality of elongated elastic members 63 is fixed in an extended state in the longitudinal direction on folded sections and surrounding sections of the doubled sheet at intervals therebetween in the width direction. The elongated elastic members 63 are not fixed at front and back ends to the barrier sheet 62, and are fixed at the middle portion to the barrier sheet 62 in such a manner that the barrier cuffs can extend and contract in the front-back direction. The barrier sheet 62 may use favorably a soft nonwoven fabric with excellent uniformity and concealment properties such as spun-bonded nonwoven fabrics (SS, SSS, and the like), SMS nonwoven fabrics (SMS, SSMMS, and the like), or melt-blown nonwoven fabrics, which are made water-repellent as required using silicon or the like. A basis weight of fibers in the fabric is preferably about 10 to 30 g/m². The elongated elastic members 63 may use rubber threads or the like. If spandex rubber threads are used, a thickness thereof is preferably 420 to 1,120 dtex, more preferably 620 to 940 dtex. The spandex rubber threads are fixed at an extension ratio of preferably 150 to 350%, more preferably 200 to 300%. In addition, although not shown, a water-proof film may be interposed in the two-folded barrier sheet.

Preferably, the inner barrier cuffs 61 each have one or two elongated elastic members 63 at the leading end thereof, and more preferably, the inner barrier cuffs 61 each have also one or two elongated elastic members 63 at an middle portion between the leading end and base end portions. With the elongated elastic members 63 as supporting points at the middle portions, the inner barrier cuffs 61 are likely to contact by surface the skin of a wearer in an area ranging from the middle to leading end portions. The inner barrier cuffs 61 have preferably the elongated elastic members 63 disposed at the middle portions in a range corresponding to 30 to 70% of height of the inner barrier cuffs 61 (the length of the projecting section in the width direction). In disposable diapers for babies and infants, the preferred height of the inner barrier cuffs 61 is about 15 to 35 mm, and therefore the inner barrier cuffs 61 each have preferably the elongated elastic members 63 disposed in an area ranging from the leading end portion toward the base end portion by 5 to 25 mm, more preferably by 12 to 18 mm. If the elongated elastic members 63 are disposed in parallel at the leading end and/or middle portions of the inner barrier cuffs 61, an interval 61d therebetween is preferably 2 to 10 mm, more preferably 2 to 6 mm.

In each of the inner barrier cuffs 61, an end of a portion on an opposite side of the folded section in the width direction is designated as an attachment section (inner attachment section) 65 that is fixed on the side portions of the inner body 200 from the top to back side surfaces; a section other than the attachment section 65 is designated as a projecting section 66 which projects from the attachment section 65 (so as to be located on the folded-back section side and constitutes an inner projecting section); both ends of the projecting section 66 in the front-back direction are fixed to the surface of the face sheet 30 by a front-back fixed portion 67 with the use of a hot-melt adhesive or heat sealing; an middle portion in the front-back direction is designated as a non-fixed free portion (inner free portion); and the elongated elastic members 63 are fixed in an extended state to the free portion in the front-back direction.

The outer barrier cuffs 60 each are basically identical in structure to the inner barrier cuffs 61, except that: an attachment section (outer attachment section) 68 is fixed to an external surface of the inner barrier cuff 61, nearer the central portion of the inner body 200 on the back side in the width direction than the attachment section 65 of the inner barrier cuff 61; both ends of a projecting section (outer projecting section) 69 in the front-back direction include a root section that passes by the side portion of the inner body 200 from the attachment section 68, extends to the surface of both ends of the inner projecting section 66 of the inner barrier cuff 61 in the front-back direction and is fixed to the surface of the both ends of the inner projecting section 66 in the front-back direction, and includes a leading end portion that is folded back from a leading end of the root section outward in the width direction and is fixed to the root section; and layout and number of the elongated elastic members 63 are different from those in the inner barrier cuffs 61.

However, similarly to the outer barrier cuffs 60, the inner barrier cuffs 61 each may also be configured in such a manner that a leading end of the inner projecting section is folded back outward in the width direction, more specifically, the leading end is folded back outward in the width direction and fixed to the root section, provided that the folded inner barrier cuffs have heights being ½ or less, preferably ⅓ or less of the inner barrier cuffs 61 (the length of the projecting section in the width direction).

The number of the elongated elastic members 63 is preferably 2 to 6, more preferably 3 to 5, at each of free portions (outer free portions) of the outer barrier cuffs 60. The interval 60d therebetween is appropriately set between 3 to 10 mm. In such an arrangement, the outer barrier cuffs 60 are likely to contact by surface the skin of a wearer in areas with the elongated elastic members 63. The outer barrier cuffs 60 may also have the elongated elastic members 63 at the root sections as well as the leading end portions. A fineness and extension ratio of the elongated elastic members 63 on the outer barrier cuffs 60 may be the same as those on the inner barrier cuffs 61. Preferably, a fineness of the elongated elastic members 63 on the outer barrier cuffs 60 is identical to or larger than those on the inner barrier cuffs 61, and an extension ratio of the elongated elastic members 63 on the outer barrier cuffs 60 is identical to or lower than those on the inner barrier cuffs 61.

In addition, it is preferred that a front-back direction length of the front-back fixed portions 67 of the projecting sections 66 and 69 in the inner barrier cuff 61 is equal to or smaller than that in the outer barrier cuff 60. It is also preferred that a front-back direction fixing length of the elongated elastic members 63 in the inner barrier cuff 61 is equal to or larger than that in the outer barrier cuff 60. Boundaries between the attachment section 65 and the projecting section 66 may be identically located in the inner barrier cuff 61 and the outer barrier cuff 60, but preferably, the boundary in the outer barrier cuff 60 is located nearer the central portion of the inner body 200 in the width direction than the boundary in the inner barrier cuff 61. In this case, a separation distance between the boundaries is preferably 10 mm or less.

Preferably, the outer barrier cuffs 60 and the inner barrier cuffs 61 each have linear root fixed portions formed with a hot-melt adhesive or by heat sealing, edges of the attachment sections 68 and 65 on the projecting sections 66 and 69 sides, respectively. In addition, other fixed portions can be fixed in appropriate patterns with a hot-melt adhesive or the like. The linear root fixed portions are preferably positioned on the top side of the inner body 200 in the vicinities of the side portions (specifically, at a position of 0 to 5 mm, preferably 0 to 3 mm, from the side edge of the inner body 200 in the width direction) or on the back side of the inner body 200. In this case, since the outer barrier cuffs 60 and the inner barrier cuffs 61 are each folded back and fixed on the top side virtually only at the both front-back ends, the barrier cuffs are erected outward in the width direction at the crotch portion which is not sufficiently affected by an action of the front-back fixed portions 67 toward the central portion of the inner body 200 in the width direction, whereby wide pockets can be formed by the inner barrier cuffs 61. If the linear root fixed portions are situated on the top side at positions of 5 mm or more from the side edges of the inner body 200 in the width direction, the barrier cuffs are erected at the crotch portion toward the central portion of the inner body 200 in the width direction, whereby narrower pockets are undesirably formed by the inner barrier cuffs 61. If the root fixed portions are to be provided on the back side, the root fixed portions are appropriately situated at positions of 0 to 20 mm from the side edges of the inner body 200, or may be situated at positions in the excess of 20 mm.

The attachment sections 68 and 65 of the outer and inner barrier cuffs 60 and 61 may be fixed to appropriate members of the inner body 200, such as the face sheet 30, the liquid impervious sheet 11, the absorbent element 50, or the like. In addition, either of the barrier cuffs may be fixed to the inner body 200 via the other barrier cuff.

In the thus configured outer and inner barrier cuffs 60 and 61, contraction forces of the elongated elastic members 63 act so as to bring the both front-back ends of the barrier cuffs closer to each other. However, the both front-back ends of the projecting sections 66 and 69 are fixed not to be erected, whereas portions between the both ends are not fixed as free portions. Accordingly, the outer and inner barrier cuffs 60 and 61 are erected such that only the free portions contact the skin of a wearer as shown in FIG. 3. In particular, with the attachment sections 68 and 65 located on the back side of the inner body 200, the outer and inner barrier cuffs 60 and 61 are erected so as to open outward in the width direction at the crotch portion and a surrounding portion thereof, and therefore the outer and inner barrier cuffs 60 and 61 contact by surface the legs of a wearer, thereby resulting in an increased fit. Meanwhile, on the both front and back sides (ventral and back sides) of the crotch portion, the outer and inner barrier cuffs 60 and 61 are restricted by the front-back fixed portions 67 so as not to open outward in the width direction, and therefore the inner barrier cuffs 61 and the lower half portions of the outer barrier cuffs 60 are erected high. This reliably prevents leakage from the both sides of the inner body 200 at the ventral and back portions. In addition, the front-back fixed portions 67 of the projecting sections 66 in the inner barrier cuffs 61 are not folded back, and the front-back fixed portions 67 of the projecting sections 68 in the outer barrier cuffs 60 are folded back outward. Accordingly, the outer and inner barrier cuffs 60 and 61 are erected reliably with a wide space therebetween in such a manner that separation of the inner and outer free portions in the outer and inner barrier cuffs 60 and 61 is maintained. As a result, the outer and inner barrier cuffs 60 and 61 are fitted individually to the legs of a wearer, thereby providing an excellent leakage preventing property.

The dimensions of the barrier cuffs 60 and 61 can be decided as appropriate. In disposable diapers for babies and infants, as shown in FIG. 7 for example, an erect height W5 of the inner barrier cuff 61 (a length of the projecting section 66 in the width direction in the open diaper) is preferably 10 to 50 mm, in particular preferably 15 to 35 mm. An erect height W6 of the outer barrier cuff 60 (a length of the projecting section 69 in the width direction of the open diaper) is preferably 15 to 60 mm, in particular preferably 20 to 40 mm. In addition, when the inner barrier cuffs 61 are folded toward the top surface of the face sheet 30, a separation distance W4 between the leading ends of the inner barrier cuffs 61 is preferably 60 to 170 mm, in particular preferably 70 to 120 mm. In addition, when the outer barrier cuffs 60 are flatly folded in parallel to the top surface of the face sheet 30, a separation distance W3 between folding lines located at innermost positions is preferably 60 to 190 mm, in particular preferably 70 to 140 mm.

Alternatively, only either of the outer and inner barrier cuffs 60 and 61 may be provided, unlike the illustrated embodiment.

In addition, if the connecting member 12x is smaller in width than the inner body 200 between the ventral side outer sheet 12F and the back side outer sheet 12B, the liquid impervious sheet 11 as a back side member of the inner body 200 is exposed on the both sides of the connecting member 12x. To eliminate such exposure, as in the illustrated example, the barrier sheet 62 of either the outer or inner barrier cuffs 60 and 61 is preferably turned from the both sides to the back surface of the inner body 200 and extended to the both sides of the connecting member 12x. Accordingly, it is possible to cover the most or entire part of the back surface of the inner body 200 even if the connecting member 12x is decreased in width. As a matter of the course, a cover sheet made of a nonwoven fabric may be provided to cover the entire liquid impervious sheet 11 exposed on the external side of the product or to cover the approximately entire back surface of the inner body 200.

(Absorbent Element)

The absorbent element 50 of this embodiment has the absorbent body 56, and the covering sheet 58 that covers the entire absorbent body 56. The covering sheet 58 may be omitted.

(Absorbent Body)

The absorbent body 56 can be formed by a fiber assembly. Such a fiber assembly is preferably hydrophilic, and may use accumulated short fibers such as fluff pulp, synthetic fibers or the like, or may use a filament aggregate that can be obtained by opening as necessary a tow (fiber bundle) of synthetic fibers constituted by cellulose acetate or the like. A basis weight of fibers may be about 120 to 200 g/m$^2$ for accumulated fluff pulp or short fibers, for example, and may be about 30 to 120 g/m$^2$ for a filament aggregate, for example. A fineness of synthetic fibers is 1 to 16 dtex, preferably 1 to 10 dtex, more preferably 1 to 5 dtex, for example. If a filament aggregate is used, filaments may be non-crimped fibers but preferably are crimped fibers. A degree of crimping of the crimped fibers may be about 5 to 75 crimps per inch, preferably about 10 to 50 crimps per inch, and more preferably about 15 to 50 crimps per inch. In many cases, uniformly crimped fibers are used.

The absorbent body 56 extends forward from a center CL in the front-back direction so as to cover 30 to 48% of entire length L5 of the article, and extends backward from the center CL in the front-back direction so as to cover 25 to 45% of the entire length L5 of the article. The absorbent body 56 may be rectangular. However, as shown in FIG. 6, the absorbent body 56 is preferably formed in the shape of a sandglass, including: a front end portion 56F; a back end portion 56B; and a narrower portion 56N that is located between the front and back end portions 56F and 56B and is narrower than the same, thereby to improve the absorbent body 56 and the barrier cuffs 60 and 61 in fit property around the legs. Assuming that a front-back direction length of the absorbent body front end portion 56F is designated as; a front-back direction length of an overlap between the absorbent body 56 and the ventral side outer sheet 12F is designated as L2; a front-back direction length of the absorbent body back end portion 56B is designated as L3; a front-back direction length of an overlap between the absorbent body 56 and the back side outer sheet 12B is designated as L4; a minimum width of the narrower portion 56N is designated as W1; and widths of the absorbent body front end portion 56F and absorbent body back end portion 56B are designated as W2, the absorbent body 56 is preferably configured so as to satisfy Equations (1) to (4) listed below.

$$70 \text{ mm} \leq W1 \leq W2 \leq 190 \text{ mm} \tag{1}$$

$$0.5 \leq W1/W2 \leq 0.85 \tag{2}$$

$$0 \text{ mm} \leq L1 - L2 \leq 70 \text{ mm} \tag{3}$$

$$0 \text{ mm} \leq L3 - L4 \leq 50 \text{ mm} \tag{4}$$

If W1 and W2 are too small, the barrier cuffs erect unstably and the absorbent body becomes insufficient in absorption amount. If W1 and W2 are too wide, the absorbent body is decreased in a fit property and therefore deteriorates wear comfort.

In addition, when the absorbent body 56 falls within the foregoing value ranges, the absorbent body 56 does not exist at the crotch portion in the vicinities of the attachment sections 65 of the barrier cuffs 60 and 61. Accordingly, the barrier cuffs 60 and 61 increase in the degree of freedom of movement. As a result, the barrier cuffs 60 and 61 become likely to open outward in the width direction and contact by surface the skin of a wearer, whereby the movements of the legs of a wearer can be more suitably followed by the fitting surfaces of the barrier cuffs 60 and 61. Since the absorbent body 56 exists in sufficient areas of the inner body 200 on the both sides at the front and back side portions, the barrier cuffs 60 and 61 are stably erected with the absorbent body 56 as a base point (supporting point). An area of the diaper ranging from the both front and back sides to the crotch portion constitutes a displacement section where the barrier cuffs 60 and 61 shift from an erected posture to an opening posture outward in the width direction with respect to the both side edges of the inner body 200 in the width direction. This posture shift of the barrier cuffs 60 and 61 is supported by the absorbent body 56 existing on the side portions of the inner body 200, whereby the barrier cuffs 60 and 61 are entirely erected in a stable manner. If the absorbent body 56 falls outside the foregoing value rages and the narrower portion is too large, the barrier cuffs 60 and 61 are excessively increased in the degree of the freedom of movement at the crotch portion, and may be likely to create a gap between the leg portions of the diaper and the legs of a wearer. In addition, the barrier cuffs 60 and 61 may be erected unstably without a base point (supporting point) at the crotch portion on the front and back sides. In contrast, if the narrower portion is too small, the barrier cuffs 60 and 61 are undesirably decreased in the degree of the freedom of movement.

Further, the front-back direction length L7 of the entire narrower portion 56N is preferably 80 mm or more, in particular preferably 120 to 260 mm. If the front-back direction length L7 of the narrower portion 56N is too short, the barrier cuffs 60 and 61 are undesirably decreased in the degree of the freedom of movement, and the absorbent body 56 decreases a fit to the legs of a wearer and interferes with the movements of the legs. If the length L7 is too long, the barrier cuffs 60 and 61 cannot erect stably.

(High-Absorbent Polymer Particles)

The absorbent body 56 preferably has high-absorbent polymer particles dispersed and held overall therein. The high-absorbent polymer particles may be not only "particles" but also "powders". A particle diameter of the high-absorbent polymer particles may be the same as that of particles used in this kind of absorbent articles, and is 1,000 µm or less, desirably in particular 150 to 400 µm. There are no particular limits on a material for the high-absorbent polymer particles, and a preferred material is 40 g/g or more in capacity of water absorption. The high-absorbent polymer particles may be based on starch, cellulose, or synthetic polymer, and may use starch-acrylic acid (salt) graft copolymer, saponified product of starch-acrylonitrile copolymer, cross-linked sodium carboxymethyl cellulose, acrylic acid (salt) polymer, or the like. A shape of the high-absorbent polymer particles is preferably a commonly used particulate shape, and may also be any other shape.

The high-absorbent polymer may be combined with an antibacterial substance. In particular, preferred high-absorbent polymer particles are antibacterial and deodorant high-absorbent polymer particles that contain zeolite particles in which some or all of ion-exchangeable ions are substituted by silver ions (hereinafter, referred to as antibacterial and deodorant zeolite) or antibacterial and deodorant high-absorbent polymer particles in which antibacterial and deodorant zeolite particles are attached by static electricity to surfaces of high-absorbent polymer particles.

The high-absorbent polymer particles preferably have a water absorption speed of 40 seconds or less. If the water absorption speed exceeds 40 seconds, a backflow phenomenon becomes prone to occur, where a liquid having been supplied to the absorbent body 56 flows back out of the absorbent body 56.

In addition, the high-absorbent polymer particles are preferably 1,000 Pa or more in gel strength. This prevents effectively a sticky feel after absorption of a liquid even if the absorbent body 56 is high in bulk.

A content of the high-absorbent polymer particles is preferably set within the range of 100 to 400 g/m$^2$, in particular 170 to 300 g/m$^2$, in such a manner that the content of the high-absorbent polymer particles is larger than a content of hydrophilic fibers, specifically, in weight comparison, with respect to 1 of the fiber assembly, the high-absorbent polymer particles becomes about 1.1 to 2.0, in particular about 1.4 to 1.6. If the polymer content is less than 170 g/m$^2$, the high-absorbent polymer particles can be used only for the purpose of training. However, if a wearer excretes urine (urination) more than once without being aware of it, the high-absorbent polymer particles may become insufficient in absorption capacity, thereby resulting in urine leakage. In contrast, if the polymer content exceeds 300 g/m$^2$, the high-absorbent polymer particles may have grainy feel and generate a sense of discomfort in a wearer.

If necessary, the high-absorbent polymer particles can be adjusted in density or amount of dispersion in the planar direction of the absorbent body 56. For example, an amount of dispersion may be made larger at a liquid excreted portion than other portions. With regard to a difference between the sexes, the dispersion density (amount) may be increased at the front side portion for men or increased at the middle portion for women. The polymer may not exist locally (for example, in spots) in the absorbent body 56 along the planar direction.

(Covering Sheet)

The covering sheet 58 may use any of tissue paper, in particular crepe paper, nonwoven fabrics, polyethylene-layered nonwoven fabrics, foraminous sheets, and the like. The covering sheet 58 desirably is a finely woven sheet so as not to let the high-absorbent polymer particles pass through. In addition, the covering sheet 58 is appropriately thin and has a low basis weight to allow a wearer to sense easily a temperature change from a face side. The covering sheet 58 preferably has a thickness of about 0.05 to 3 mm, in particular 0.2 mm or less, and a basis weight of about 5 to 25 g/m$^2$, in particular 15 g/m$^2$ or less, for excellent heat transfer performance from the back side to the skin of a wearer. If any nonwoven fabric is used for the covering sheet 58, nonwoven fabrics processed by a spun-bonding method and an SMS method, in particular, nonwoven fabrics processed by an SMS method, are preferred for balanced thinness and strength. Materials for such nonwoven fabrics may use polypropylene or polyethylene/polypropylene.

As in the illustrated embodiment, if there is a seam of the covering sheet 58 on an external side (facing the skin of a wearer) of the absorbent element 50, it is preferred that overlapping width 58W of the seam is smaller than width 40W of a disposition region of a temperature changing substance 40, and is 40 mm or less, in particular 20 mm or less for allowing a wearer to sense a temperature change effectively. If the seam is made narrow in this manner, the high-absorbent polymer particles do not slip out of the covering sheet 58 for the reason described above. In addition, the seam of the covering sheet 58 is preferably formed near a side portion of the covering sheet 58 so as not to include the widthwise center contacting an urination point.

<Example of a Method for Manufacturing an Underpants Type Disposable Diaper>

Figure 10:
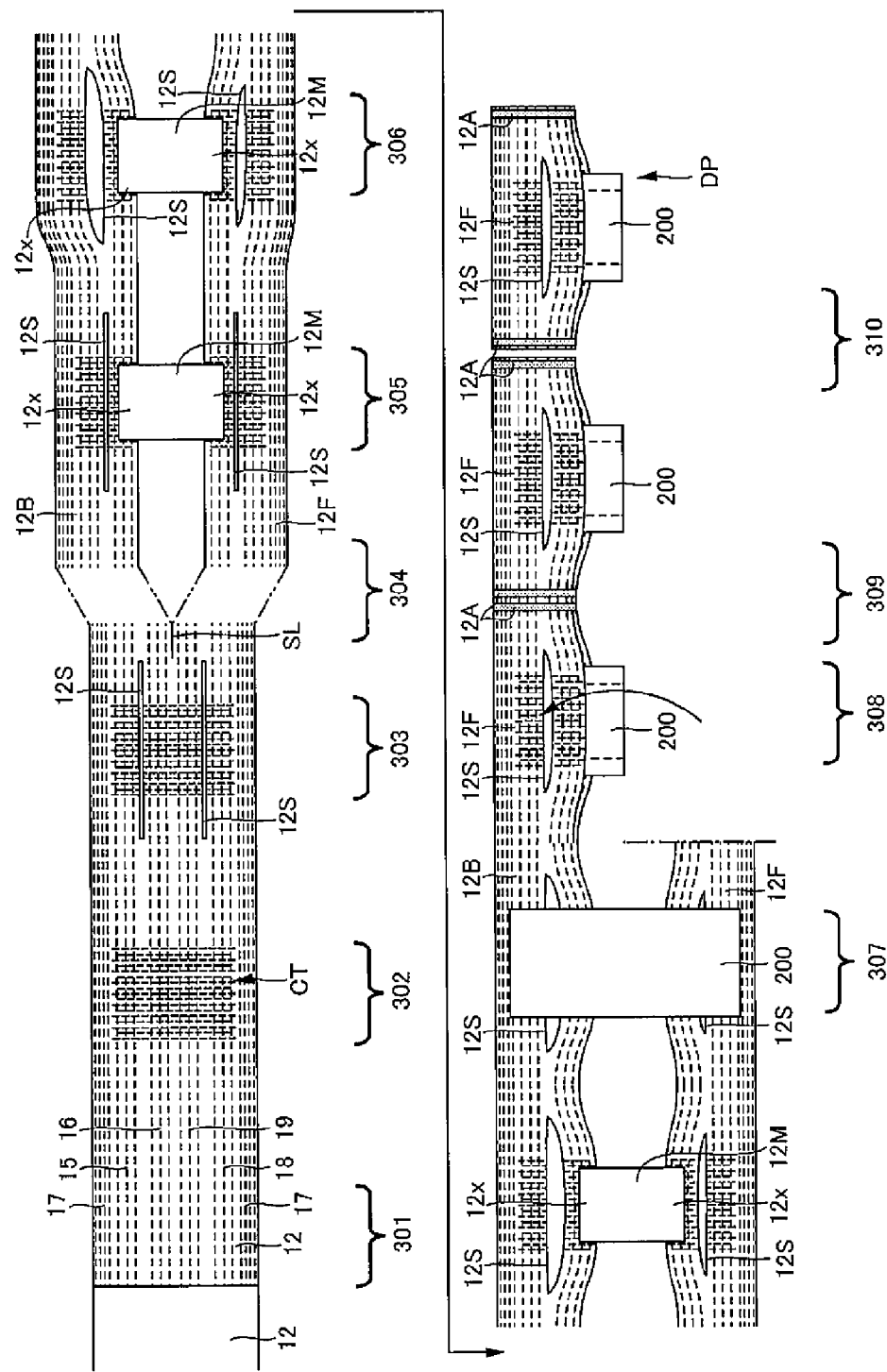
FIG. 10 is a plane view of a flow of a manufacturing process.
Figure 11:
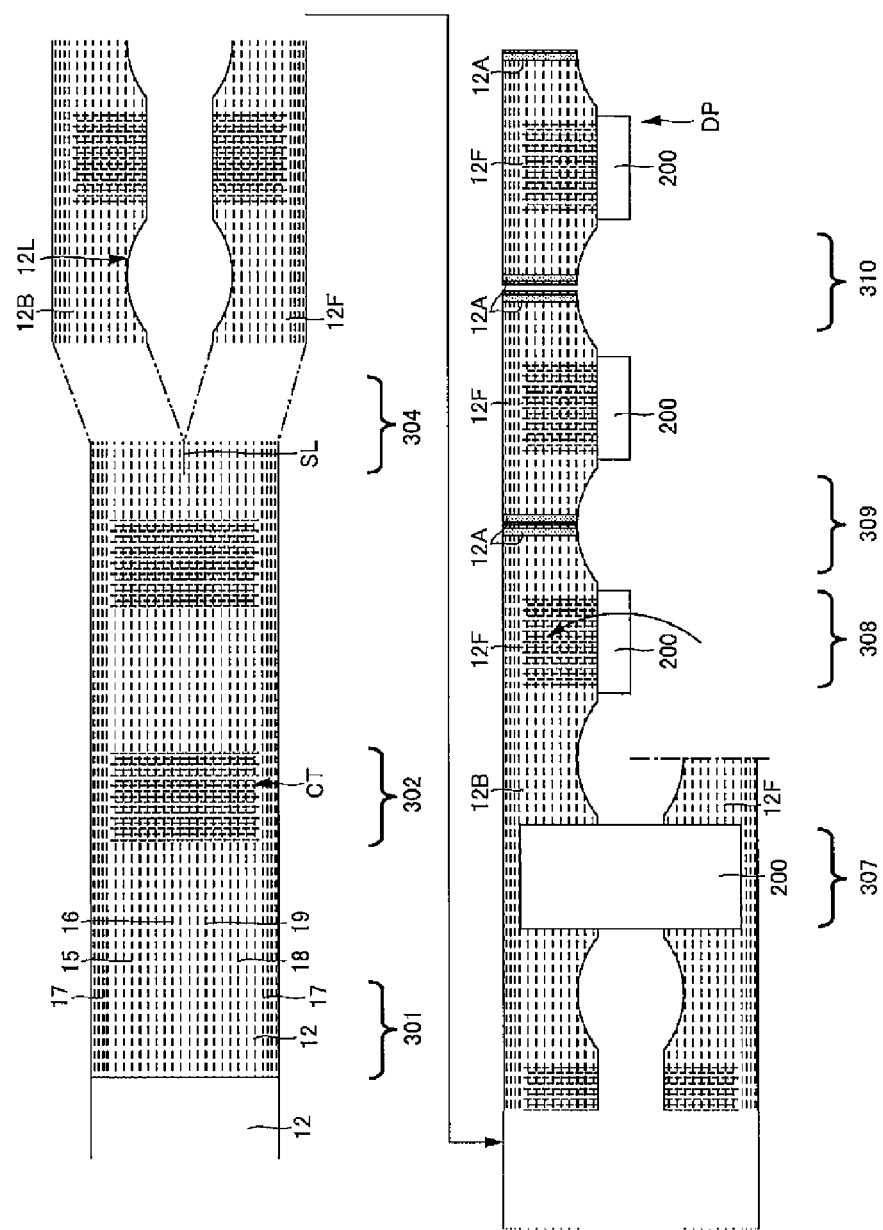
FIG. 11 is a plane view of a flow of a conventional manufacturing process.

FIG. 10 shows an example of a method for manufacturing an underpants type disposable diaper described above. This manufacturing line is configured to convey diapers in a lateral direction such that a width of each diaper is oriented along a machine direction (MD) or line flow direction. In this line, portions to be the outer sheets 12F and 12B constituting the abdomen portion are formed, and the inner body 200 fabricated in another line is attached to the portions to be the outer sheets 12F and 12B. For easy understanding, not separated members in the process of manufacture will be described using the same reference numerals as those given to the separated members in a finished product.

To describe in more detail, this manufacturing line includes a elastic member attaching step 301, an elastic member cutting step 302, a separated portion forming step 303, an outer sheet cutting/splitting step 304, a connecting step 305, a widening step 306, an inner body attaching step 307, a folding step 308, a side potion joining step 309, and a separating step 310. Among these steps, the separated portion forming step 303, the connecting step 305, and the widening step 306 are characteristic as compared with the steps of a conventional manufacturing line.

Specifically, at the elastic member attaching step 301, a belt-like sheet base material 12 of a predetermined width is conveyed along a direction of continuation thereof while elongated elastic members 15 to 19 such as rubber threads are fixed in a state of being stretched in the MD direction to the approximately entire belt-like sheet base material 12 at intervals in the CD direction, and another belt-like sheet base material 12 of a predetermined width is supplied in a direction of continuation thereof and is attached to a top surface of the former sheet base material 12. Among the elongated elastic members, the members situated on the outside in the CD direction with respect to the separated portion described later constitute the first elongated elastic members 15 and 18, and the members situated at the center in the CD direction of the sheet base material constitute the second elongated elastic members. In addition, if necessary, the elastic member cutting step 302 is performed to cut the elastic members 15, 16, 18, and 19 positioned in a section CT which will overlap the inner body 200, at predetermined intervals in the MD direction, using a cutting device such as a heat embosser or the like, so that the elastic members 15, 16, 18, and 19 do not act stretching force on the section CT. The cutting portions are equivalent to the portions with reference numeral 12c.

Next, at the separated portion forming step 303, separated portions 12S as slits or elongated openings are formed so as to extend in the MD direction in the portion to be the ventral side outer sheet 12F and the portion to be the back side outer sheet 12B at middle portions in the CD direction of central regions in the MD direction. The separated portion forming step 303 may be performed concurrently with or subsequent to the outer sheet cutting/splitting step 304 described later.

Next, at the outer sheet cutting/splitting step 304, the belt-like sheet base material 12 is cut by a slitter at a predetermined site SL of the middle portion in CD direction to split into the portion to be the ventral side outer sheet 12F and the portion to be the back side outer sheet 12B, and a space between the outer sheets 12F and 12B is increased to a predetermined distance. After the slitting, if necessary, end edges on the center side in the CD direction of the outer sheets 12F and 12B (edges of the leg openings LO) may be cut off in a curved line. However, the cutting is not performed if trim loss needs to be completely eliminated. Nevertheless, the edges of the leg openings LO can be diagonally fitted to the legs of a wearer as described later. In addition, in the illustrated example, the portion to be the ventral side outer sheet 12F and the portion to be the back side outer sheet 12B are first integrally formed and then split at the outer sheet cutting/splitting step 304. Alternatively, the portion to be the ventral side outer sheet 12F and the portion to be the back side outer sheet 12B can be formed by separate sheet base materials from the first, thereby to omit the outer sheet cutting/splitting step 304.

Next, at the connecting step 305, the connecting member 12M is used to connect the portion to be the ventral side outer sheet 12F and the portion to be the back side outer sheet 12B at the middle portions in the MD direction on the center sides in the CD direction with respect to the separated portions 12S. This connection can be made by using appropriate joint means such as a hot-melt adhesive or heat sealing. In addition, the connecting step 305 is performed subsequent to both the separated portion forming step 303 and the outer sheet cutting/splitting step 304.

At the widening step 306 subsequent to the connecting step 305, the portion to be the ventral side outer sheet 12F and the portion to be the back side outer sheet 12B are pulled up at entire sections in the MD direction on the outside in the CD direction with respect to the separated portions 12S, and at sections on the center side in the CD direction with respect to the separated portions 12S and at the same time on the both sides of connecting portions 12x connected to the connecting member 12M in the MD direction, toward the outside in the CD direction of the connecting portions 12x connected to the connecting member 12M. Then, while the separated portions 12S are deformed with increasing separation distances in the CD direction thereof, the portion to be the ventral side outer sheet 12F and the portion to be the back side outer sheet 12B are extended at the entire sections in the MD direction on the outside in the CD direction with respect to the separated portions 12S to the outside in the CD direction, horizontally toward the outside in the CD direction, and the portion to be the ventral side outer sheet 12F and the portion to be the back side outer sheet 12B are extended diagonally at sections on the center side in the CD direction with respect to the separated portions 12S and at the same time on the both sides in the MD direction of the connecting portions 12x connected to the connecting member 12M, so as to come closer to the outside in the CD direction with increasing proximity to the both sides in the MD direction. Edges on the center side in the CD direction of the diagonally pulled portions constitute the edges of the leg openings LO.

After that, at the inner body attaching step 307, the inner body 200 fabricated in advance in another line is supplied at predetermined intervals in the MD direction and is fixed to the portion to be the ventral side outer sheet 12F and the portion to be the back side outer sheet 12B so as to straddle the two portions.

In addition, at the folding step 308, the portion to be the ventral side outer sheet 12F and the portion to be the back side outer sheet 12B are folded in the CD direction such that attachment surfaces thereof to be attached to the inner body 200 overlap together. Then, at the side portion joining step 309, the portion to be the ventral side outer sheet 12F and portion to be the back side outer sheet 12B are joined together at both sides of individual diapers. Next, at the separating step 310, the portion to be the ventral side outer sheet 12F and the portion to be the back side outer sheet 12B are cut at boundaries between individual diapers, thereby obtaining individual diapers DP.

In the thus manufactured disposable diaper, the edges of the leg openings LO are formed by the diagonally extended portions at the both sides of the connecting portions 12x so as to fit the groin and gluteal portions of a wearer. In addition, the diaper does not need to be cut at the leg openings, thereby causing no or significantly less trim loss than that of conventional diapers. Further, when the second elongated elastic members 16 and 19 are simply attached in the MD direction, the second elongated elastic members 16 and 19 in a product state can be situated along the width direction at positions overlapping the connecting portion 12x and can be situated along the leg openings LO on the both sides of the connecting portions 12x, without the need to use a waving device. This allows the diaper leg openings LO to favorably fit the legs of a wearer.

INDUSTRIAL APPLICABILITY

The present invention is applicable to an underpants type disposable diaper and a method for manufacturing the same.

BRIEF DESCRIPTION OF NUMERALS

100 . . . Abdomen portion, 11 . . . Liquid impervious sheet, 12F . . . Ventral side outer sheet, 12B . . . Back side outer sheet, 200 . . . Inner body, 30 . . . Face sheet, 50 . . . Absorbent element, 56 . . . Absorbent body, 58 . . . Covering sheet, 60 . . . Side barrier cuffs, 62 . . . Barrier sheet, 12S . . . Separated portion, 12M . . . Connecting member, 12x . . . Connecting portion, 12v . . . Fixing portion.

The invention claimed is:

1. A disposable diaper, comprising:
a barrel shaped abdomen portion that is formed by joining together a ventral side outer sheet and a back side outer sheet, the ventral side outer sheet and the back side outer sheet each including lateral sides, a crotch side, and a waist side, the ventral side outer sheet and the back side outer sheet being joined at the respective lateral sides thereof; and
an inner body for absorbing excrement that is disposed on a portion of an inner surface of the ventral side outer sheet and disposed on a portion of an inner surface of the back side outer sheet, and said inner body being positioned between a widthwise middle portion of the ventral side outer sheet and a widthwise middle portion of the back side outer sheet;
the ventral side outer sheet and the back side outer sheet being separated at their respective crotch sides, wherein
the ventral side outer sheet and the back side outer sheet each have a an elongated opening extending in a width direction at a lengthwise middle section in the widthwise middle portion of the respective sheets,
a connecting member connecting the ventral side outer sheet to the back side outer sheet, the connecting member being attached to the ventral side outer sheet at the widthwise middle portion on the crotch side with respect to the elongated opening and the connecting member being attached to the back side outer sheet at the widthwise middle portion on the crotch side with respect to the elongated opening,
front and back end portions of the inner body are attached to the ventral side outer sheet at a section on the waist side with respect to the elongated opening, and to the back side outer sheet at a section on the waist side with respect to the elongated opening, respectively, and
the elongated openings in said ventral side outer sheet and said back side outer sheet are maintained in an at least partially open position by tension created by said connecting member being attached to the ventral side outer sheet and the back side outer sheet on the crotch side with respect to the elongated opening and said inner body being attached to the ventral side outer sheet and the back side outer sheet on the waist side with respect to the elongated opening, wherein the ventral side outer sheet and the back side outer sheet define a portion of leg openings of the disposable diaper.

2. The disposable diaper according to claim 1, wherein a first elongated elastic member is fixed in the width direction in a longitudinally stretched state to the ventral side outer sheet and the back side outer sheet on the waist side with respect to the elongated openings, and a second elongated elastic member is fixed in a longitudinally stretched state to the ventral side outer sheet and the back side outer sheet in the width direction at positions overlapping the connecting portions and in the diagonal direction on the both sides of the connecting portions, on the crotch side with respect to the elongated openings.

3. The disposable diaper according to claim 2, wherein the second elongated elastic member is thicker than the first elongated elastic member, and is fixed at a lower extension ratio than that of the first elongated elastic member.

* * * * *